(12) United States Patent
Marble et al.

(10) Patent No.: US 9,855,559 B2
(45) Date of Patent: Jan. 2, 2018

(54) MICROORGANISM NUCLEIC ACID PURIFICATION FROM HOST SAMPLES

(71) Applicant: Abbott Molecular Inc.

(72) Inventors: Herbert A. Marble, Naperville, IL (US); Thomas Laffler, Vista, CA (US)

(73) Assignee: ABBOTT MOLECULAR INC., Des Plaines, IL (US)

( * ) Notice: Subject to any disclaimer, the term of this patent is extended or adjusted under 35 U.S.C. 154(b) by 329 days.

(21) Appl. No.: 13/724,527

(22) Filed: Dec. 21, 2012

(65) Prior Publication Data

US 2013/0184446 A1 Jul. 18, 2013

Related U.S. Application Data (60) Provisional application No. 61/582,035, filed on Dec. 30, 2011.

(51) Int. Cl.
| | |
|---|---|
| *C12P 19/34* | (2006.01) |
| *B01L 7/00* | (2006.01) |
| *C07H 21/00* | (2006.01) |
| *B01L 3/00* | (2006.01) |
| *C12Q 1/68* | (2006.01) |

(52) U.S. Cl.
CPC ........... *B01L 7/54* (2013.01); *B01L 3/502784* (2013.01); *B01L 7/525* (2013.01); *C07H 21/00* (2013.01); *C12P 19/34* (2013.01); *C12Q 1/686* (2013.01); *B01L 2400/0415* (2013.01); *B01L 2400/0433* (2013.01); *B01L 2400/0445* (2013.01); *B01L 2400/086* (2013.01)

(58) Field of Classification Search
None
See application file for complete search history.

(56) References Cited

U.S. PATENT DOCUMENTS

| | | | | |
|---|---|---|---|---|
| 4,639,243 | A | * | 1/1987 | Schmidt ................. A61M 1/30 604/6.04 |
| 5,076,933 | A | | 12/1991 | Glenn et al. |
| 5,210,015 | A | | 5/1993 | Gelfand et al. |
| 5,538,848 | A | | 7/1996 | Livak et al. |
| 5,605,798 | A | | 2/1997 | Koester |
| 5,695,934 | A | | 12/1997 | Brenner |
| 5,714,330 | A | | 2/1998 | Brenner et al. |

(Continued)

FOREIGN PATENT DOCUMENTS

| | | |
|---|---|---|
| WO | 9722719 A1 | 6/1997 |
| WO | 0018957 A1 | 4/2000 |

(Continued)

OTHER PUBLICATIONS

"Viruses" (Wikipedia.com, accessed Nov. 24, 2012).*

(Continued)

*Primary Examiner* — Joseph G. Dauner
(74) *Attorney, Agent, or Firm* — David A. Casimir; Casimir Jones, S.C.

(57) ABSTRACT

The present disclosure provides systems, devices, and methods for purifying microorganism nucleic acid from a host sample, such as a whole blood sample from a human. In certain embodiments, devices and systems with multiple filters are employed and provide for the selective removal of blood cells and host nucleic acids from a sample in order to enrich for microorganism nucleic acid.

14 Claims, 2 Drawing Sheets

(56) References Cited

U.S. PATENT DOCUMENTS

| | | | |
|---|---|---|---|
| 5,750,341 A | 5/1998 | MacEvicz | |
| 5,777,324 A | 7/1998 | Hillenkamp | |
| 5,863,736 A | 1/1999 | Haaland | |
| 5,912,148 A | 6/1999 | Eggerding | |
| 5,945,283 A | 8/1999 | Kwok et al. | |
| 6,043,031 A | 3/2000 | Koester et al. | |
| 6,074,183 A * | 6/2000 | Allen | B01D 35/26 |
| | | | 210/416.1 |
| 6,130,073 A | 10/2000 | Eggerding | |
| 6,168,718 B1 * | 1/2001 | Sutter | B01D 63/081 |
| | | | 210/436 |
| 6,210,891 B1 | 4/2001 | Nyren et al. | |
| 6,258,568 B1 | 7/2001 | Nyren | |
| 6,306,597 B1 | 10/2001 | MacEvicz | |
| 6,432,360 B1 | 8/2002 | Church | |
| 6,485,944 B1 | 11/2002 | Church et al. | |
| 6,511,803 B1 | 1/2003 | Church et al. | |
| 6,787,308 B2 | 9/2004 | Balasubramanian et al. | |
| 6,833,246 B2 | 12/2004 | Balasubramanian | |
| 6,969,488 B2 | 11/2005 | Bridgham et al. | |
| 7,108,974 B2 | 9/2006 | Ecker et al. | |
| 7,115,400 B1 | 10/2006 | Adessi et al. | |
| 7,170,050 B2 | 1/2007 | Turner et al. | |
| 7,302,146 B2 | 11/2007 | Turner et al. | |
| 7,313,308 B2 | 12/2007 | Turner et al. | |
| 7,315,019 B2 | 1/2008 | Turner et al. | |
| 7,329,492 B2 | 2/2008 | Hardin et al. | |
| 7,405,281 B2 | 7/2008 | Xu et al. | |
| 7,608,399 B2 | 10/2009 | Reed et al. | |
| 7,718,361 B2 | 5/2010 | Baron et al. | |
| 7,718,421 B2 | 5/2010 | Chen et al. | |
| 7,807,360 B2 | 10/2010 | Kim et al. | |
| 7,884,201 B2 | 2/2011 | Inomata et al. | |
| 7,893,251 B2 | 2/2011 | Lorenz | |
| 7,939,249 B2 | 5/2011 | Parthasarathy et al. | |
| 7,939,300 B2 | 5/2011 | Mitsuhashi | |
| 8,017,322 B2 | 9/2011 | Ecker et al. | |
| 8,017,340 B2 | 9/2011 | Collier et al. | |
| 8,017,743 B2 | 9/2011 | Ecker et al. | |
| 8,043,811 B2 | 10/2011 | Danks et al. | |
| 8,062,533 B2 * | 11/2011 | Dawson | 210/787 |
| 2001/0046452 A1 | 11/2001 | Roback et al. | |
| 2003/0170678 A1 * | 9/2003 | Tanzi | C12Q 1/6883 |
| | | | 435/6.11 |
| 2005/0112581 A1 * | 5/2005 | Gocke | C07K 14/47 |
| | | | 435/6.11 |
| 2005/0130173 A1 | 6/2005 | Leamon et al. | |
| 2006/0234210 A1 * | 10/2006 | Kenan | A61M 1/3633 |
| | | | 435/5 |
| 2007/0036511 A1 | 2/2007 | Lundquist et al. | |
| 2007/0043317 A1 | 2/2007 | Sugawara | |
| 2007/0072196 A1 | 3/2007 | Xu et al. | |
| 2007/0077564 A1 | 4/2007 | Roitman et al. | |
| 2007/0128133 A1 | 6/2007 | Eid et al. | |
| 2007/0134128 A1 | 6/2007 | Korlach | |
| 2007/0141598 A1 | 6/2007 | Turner et al. | |
| 2007/0161017 A1 | 7/2007 | Eid et al. | |
| 2007/0188750 A1 | 8/2007 | Lundquist et al. | |
| 2007/0196846 A1 | 8/2007 | Hanzel et al. | |
| 2007/0206187 A1 | 9/2007 | Lundquist et al. | |
| 2007/0231804 A1 | 10/2007 | Korlach et al. | |
| 2007/0238679 A1 | 10/2007 | Rank et al. | |
| 2007/0250274 A1 | 10/2007 | Volkov et al. | |
| 2008/0009007 A1 | 1/2008 | Lyle et al. | |
| 2008/0030628 A1 | 2/2008 | Lundquist et al. | |
| 2008/0032301 A1 | 2/2008 | Rank et al. | |
| 2008/0050747 A1 | 2/2008 | Korlach et al. | |
| 2008/0080059 A1 | 4/2008 | Dixon et al. | |
| 2008/0095488 A1 | 4/2008 | Foquet et al. | |
| 2008/0102493 A1 | 5/2008 | Ongena et al. | |
| 2008/0108082 A1 | 5/2008 | Rank et al. | |
| 2008/0128627 A1 | 6/2008 | Lundquist et al. | |
| 2008/0145278 A1 | 6/2008 | Korlach | |
| 2008/0152280 A1 | 6/2008 | Lundquist et al. | |
| 2008/0152281 A1 | 6/2008 | Lundquist et al. | |
| 2008/0153095 A1 | 6/2008 | Williams et al. | |
| 2008/0153100 A1 | 6/2008 | Rank et al. | |
| 2008/0157005 A1 | 7/2008 | Lundquist et al. | |
| 2008/0160531 A1 | 7/2008 | Korlach | |
| 2008/0165346 A1 | 7/2008 | Lundquist et al. | |
| 2008/0176241 A1 | 7/2008 | Eid et al. | |
| 2008/0176316 A1 | 7/2008 | Eid et al. | |
| 2008/0176769 A1 | 7/2008 | Rank et al. | |
| 2008/0199874 A1 | 8/2008 | Otto et al. | |
| 2008/0199932 A1 | 8/2008 | Hanzel et al. | |
| 2008/0206764 A1 | 8/2008 | Williams et al. | |
| 2008/0212960 A1 | 9/2008 | Lundquist et al. | |
| 2008/0241951 A1 | 10/2008 | Battulga et al. | |
| 2009/0035777 A1 | 2/2009 | Kokoris et al. | |
| 2010/0051550 A1 | 3/2010 | Mitterer et al. | |
| 2011/0294122 A1 | 12/2011 | Ma et al. | |
| 2011/0294199 A1 | 12/2011 | Bearinger et al. | |
| 2011/0300609 A1 | 12/2011 | Lim et al. | |

FOREIGN PATENT DOCUMENTS

| | | |
|---|---|---|
| WO | 2006084132 A2 | 8/2006 |
| WO | 2010009415 A1 | 1/2010 |
| WO | 2010039987 A1 | 4/2010 |
| WO | 2010128100 A1 | 11/2010 |
| WO | 2011124709 A1 | 10/2011 |
| WO | 2011150115 A2 | 12/2011 |

OTHER PUBLICATIONS

"How many species of bacteria are there" (wisegeek.com; accessed Sep. 23, 2011).*

"Mammal," (Wikipedia.com; accessed Sep. 22, 2011).*

"Murinae," (Wikipedia.com, accessed Mar. 18, 2013).*

"Insect," (Wikipedia.com; accessed Mar. 8, 2013).*

"Human Hybrids," by Michael F. Hammer, Scientific American, May 2013, pp. 66-71.*

"Custon Antibody Services," PrecisionAntibody.com; accessed Apr. 16, 2014.*

Stroun et al. Annals of the New York Academy of Sciences. 2001. 945:258-264.*

Adessi C., et al., "Solid Phase DNA Amplification: Characterisation of Primer Attachment and Amplification Mechanisms," Nucleic Acids Research, 2000, vol. 28 (20), pp. E87.

Astier Y., et al., "Toward Single Molecule DNA Sequencing: Direct Identification of Ribonucleoside and Deoxyribonucleoside 5'-monophosphates by Using an Engineered Protein Nanopore Equipped with a Molecular Adapter," Journal of the American Chemical Society, 2006, vol. 128 (5), pp. 1705-1710.

Bennett S.T., et al., "Toward the 1,000 Dollars Human Genome," Pharmacogenomics, 2005, vol. 6 (4), pp. 373-382.

Birren B., et al., eds., Genome Analysis—A Laboratory Manual, vol. 1 & 2, Cold Spring Harbor Laboratory Press, 1998, Table of Contents.

Brenner S., et al., "Gene Expression Analysis by Massively Parallel Signature Sequencing (MPSS) on Microbead Arrays," Nature Biotechnology, 2000, vol. 18 (6), pp. 630-634.

Compton J., "Nucleic Acid Sequence-Based Amplification," Nature, 1991, vol. 350 (6313), pp. 91-92.

Gibson U.E., et al., "A Novel Method for Real Time Quantitative RT-PCR," Genome Research, 1996, vol. 6 (10), pp. 995-1001.

Heid C.A., et al., "Real Time Quantitative PCR," Genome Research, 1996, vol. 6 (10), pp. 986-994.

Holland P.M., et al., "Detection of Specific Polymerase Chain Reaction Product by Utilizing the 5'-3' Exonuclease Activity of Thermus Aquaticus DNA Polymerase," Proceedings of the National Academy of Sciences, 1991, vol. 88 (16), pp. 7276-7280.

International Search Report and Written Opinion for Application No. PCT/US12/71301, dated Mar. 5, 2013, 10 pages.

Korlach J., et al., "Selective Aluminum Passivation for Targeted Immobilization of Single DNA Polymerase Molecules in Zero-Mode Waveguide Nanostructures," Proceedings of the National Academy of Sciences, 2008, vol. 105 (4), pp. 1176-1181.

(56) References Cited

OTHER PUBLICATIONS

Livak K.J., et al., "Oligonucleotides with Fluorescent Dyes at Opposite Ends Provide a Quenched Probe System Useful for Detecting PCR Product and Nucleic Acid Hybridization," PCR Methods and Applications, 1995, vol. 4 (6), pp. 357-362.
MacLean D., et al., "Application of 'next-generation' Sequencing Technologies to Microbial Genetics," Nature Reviews Microbiology, 2009, vol. 7 (4), pp. 287-296.
Margulies M., et al., "Genome Sequencing in Microfabricated High-Density Picolitre Reactors," Nature, 2005, vol. 437 (7057), pp. 376-380.
Mitra R.D., et al., "Fluorescent in Situ Sequencing on Polymerase Colonies," Analytical Biochemistry, 2003, vol. 320 (1), pp. 55-65.
Neri B.P., et al., "Transferring Automation for Large-scale Development and Production of InvaderTM SNP Assays," in Advances in Nucleic Acid and Protein Analyses, 2000, vol. 3926, pp. 117-125.
Piatek A.S., et al., "Molecular Beacon Sequence Analysis for Detecting Drug Resistance in *Mycobacterium tuberculosis*," Nature Biotechnology, 1998, vol. 16 (4), pp. 359-363.
Shendure J., et al., "Accurate Multiplex Polony Sequencing of an Evolved Bacterial Genome," Science, 2005, vol. 309 (5741), pp. 1728-1732.
Sohn L.L., et al., "Capacitance Cytometry: Measuring Biological Cells One by One," Proceedings of the National Academy of Sciences, 2000, vol. 97 (20), pp. 10687-10690.
Thelwell N., et al., "Mode of Action and Application of Scorpion Primers to Mutation Detection," Nucleic Acids Research, 2000, vol. 28 (19), pp. 3752-3761.
Tyagi S., et al., "Molecular Beacons: Probes that Fluoresce Upon Hybridization," Nature Biotechnology, 1996, vol. 14 (3), pp. 303-308.
Tyagi S., et al., "Multicolor Molecular Beacons for Allele Discrimination," Nature Biotechnology, 1998, vol. 16 (1), pp. 49-53.
Voelkerding K.V., et al., "Next-Generation Sequencing: from Basic Research to Diagnostics," Clinical Chemistry, 2009, vol. 55 (4), pp. 641-658.
Supplementary European search report for Application No. EP12863486, dated Apr. 25, 2016.

* cited by examiner

FIG. 1

MULTI-STAGE PURIFICATION FILTER

FIG. 2

MICROFLUIDIC EXTRACTION DEVICE

WHOLE BLOOD

TARGET DNA
OR
RNA

A = ~10-20 µM PORE SIZE
B = ~1-2 µM PORE SIZE
C = ~0.1 µM PORE SIZE
D = AFFINITY CAPTURE ZONE (SELECT AGAINST HUMAN GENOME DNA)

STAND ALONE OR MODULAR

MICROORGANISM NUCLEIC ACID PURIFICATION FROM HOST SAMPLES

The present application claims priority to U.S. provisional application Ser. No. 61/582,035, filed Dec. 30, 2011, which is herein incorporated by reference in its entirety.

FIELD OF THE INVENTION

The present disclosure relates to systems, devices, and methods for purifying microorganism nucleic acid from a host sample, such as a whole blood sample from a human. In certain embodiments, devices and systems with multiple filters are employed and provide for the selective removal of blood cells and host nucleic acids from a sample in order to enrich for microorganism nucleic acid.

BACKGROUND

Nucleic acid detection methods are very sensitive. Such methods, however, generally require some level of upstream sample preparation or processing. For example, enrichment or purification of the nucleic acid from other components present in the sample is typically required. Such components can cause nucleic acid degradation, inhibition of nucleic acid detection, and even masking of nucleic acid detection. The level of sample preparation required can render nucleic acid detection outside of a laboratory difficult. Transport of samples to a laboratory for nucleic acid detection also can be difficult. For example, samples should generally be collected under sterile conditions in order to minimize contamination and sample degradation. Refrigeration, freezing, and the addition of preservatives and/or stabilizers also should generally be employed to minimize and delay sample degradation.

Methods of separating nucleic acid from other components in a crude liquid sample are described in U.S. Pat. No. 8,043,811 (herein incorporated by reference). Method of extracting nucleic acid from cells, amplifying segments of nucleic acid, and detecting nucleic acid are disclosed in U.S. Pat. No. 8,017,340 (herein incorporated by reference). A high through-put method and a device for isolating and quantifying mRNA directly from whole blood are disclosed in U.S. Pat. No. 7,939,300 (herein incorporated by reference). Methods of separating nucleic acid inhibitors in a sample are disclosed in U.S. Pat. No. 7,939,249 (herein incorporated by reference). Methods for the selective isolation of nucleic acid from microbial cells that are present in a composite sample comprising higher eukaryotic cells and/or tissues are disclosed in U.S. Pat. No. 7,893,251 (herein incorporated by reference). Methods for separating and purifying RNA are disclosed in U.S. Pat. No. 7,884,201 (herein incorporated by reference). A sample processing apparatus is disclosed in U.S. Pat. No. 7,718,421 (herein incorporated by reference). Methods for detecting the presence of a bacterial pathogen in a clinical sample, such as whole blood, are disclosed in U.S. Pat. No. 7,718,361 (herein incorporated by reference). Methods for determining the quantity of nucleic acids in a sample are disclosed in U.S. Pat. No. 7,608,399 (herein incorporated by reference). U.S. Pat. Pub. 2011/0300609 (herein incorporated by reference) discloses a nucleic acid extracting apparatus. U.S. Pat. App. Pub. No. 2011/0294199 (see, also, U.S. Pat. Pub. No. 2011/0294122 and WO 2011/150115; all of which are herein incorporated by reference) discloses an apparatus for detecting a nucleic acid in a sample. WO 2011/124709 (herein incorporated by reference) discloses a chromatographic device for isolating and purifying nucleic acids from contaminants by gel filtration chromatography. WO 2010/039987 (herein incorporated by reference) discloses a method for detecting nucleic acids in a blood sample.

SUMMARY OF THE INVENTION

The present disclosure provides systems, devices, and methods for purifying microorganism nucleic acid from a host sample, such as a whole blood sample from a human. In certain embodiments, devices and systems with multiple filters are employed and provide for the selective removal of blood cells and host nucleic acids from a sample in order to enrich for microorganism nucleic acid.

In certain embodiments, the present disclosure provides multi-stage purification devices comprising: a) a sample containment vessel, wherein the sample containment vessel comprises an proximal end and a distal end, b) a first filter comprising pores approximately 10-20 µm in size, positioned inside the vessel; c) a second filter comprising pores approximately 1-2 µm in size, positioned inside the vessel and distal to the first filter; and d) a third filter comprising pores approximately 0.1 µm in size, positioned inside the vessel distal to the first and second filters; wherein the first, second, and third filters are further positioned inside the sample containment vessel such that fluid passing from the proximal end to the distal end of the sample containment vessel passes through the first, second, and third filters.

In some embodiments, the present disclosure provides multi-stage purification devices comprising: a) a sample containment vessel, wherein the sample containment vessel comprises an proximal end and a distal end, b) a first filter comprising pores approximately 10-20 µm in size (e.g., about 10, 11, 12, 13, 14, 15, 16, 17, 18, 19, or 20 µm in size) positioned inside the vessel; c) a second filter comprising pores approximately 1-2 µm in size (e.g., about 1.0, 1.1, 1.2, 1.3, 1.4, 1.5, 1.6, 1.7, 1.8, 1.0, or 2.0 µm in size), positioned inside the vessel and distal to the first filter; and d) a third filter comprising pores approximately 0.1 µm in size (e.g., 0.05, 0.06, 0.07, 0.08, 0.09, 0.1, 0.11, 0.12, 0.13, 0.14, 0.15, or 0.16 µm in size), positioned inside the vessel distal to the first and second filters; wherein the first, second, and third filters are further positioned inside the sample containment vessel such that fluid passing from the proximal end to the distal end of the sample containment vessel passes through the first, second, and third filters.

In additional embodiments, the present invention provides multi-stage purification devices comprising: a) a sample containment vessel (e.g., configured to be inserted into a centrifuge or agitation device), wherein said sample containment vessel comprises an proximal end and a distal end, b) a first filter comprising pores approximately 10-20 µm in size, positioned inside said vessel; c) a second filter comprising pores approximately 1-2 µm in size, positioned inside said vessel and distal to said first filter; d) a third filter comprising pores approximately 0.1 µm in size, positioned inside said vessel distal to said first and second filters; wherein said first, second, and third filters are further positioned inside said sample containment vessel such that fluid passing from said proximal end to said distal end of said sample containment vessel passes through said first, second, and third filters; and e) an affinity capture filter comprising affinity binding molecules, wherein said affinity capture filter is positioned inside said vessel distal to said first, second, and third filters, and further positioned such that said fluid passing from said open proximal end to said closed distal end of said sample containment vessel passes through said affinity capture filter.

The filters described herein can be used in any and every combination in the devices, systems, and methods herein. For example, the devices and systems of the present invention can have only, or at least: the first and second filters; the second and third filters; the first and third filters; of the first, second, and third filters. Any of these combinations may include, or not include, an affinity capture filter.

In certain embodiments, the devices further comprise an affinity capture filter comprising affinity binding molecules, wherein the affinity capture filter is positioned inside the vessel distal to the first, second, and third filters, and further positioned such that the fluid passing from the open proximal end to the closed distal end of the sample containment vessel passes through the affinity capture filter. In additional embodiments, the affinity binding molecules comprise human repetitive nucleic acid sequences (e.g., RNA and DNA). In other embodiments, the sample containment vessel is configured to be inserted into a centrifuge or agitation device. In other embodiments, the sample containment vessel has a tube-type shape. In further embodiments, the proximal end is open and the distal end is closed.

In some embodiments, the present disclosure provides methods of purifying a sample comprising: a) providing: i) a sample comprising human cells and suspected of containing pathogens comprising pathogen nucleic acid; and ii) a multi-stage purification device comprising: A) a sample containment vessel (e.g., configured to be inserted into a centrifuge or agitation device), wherein the sample containment vessel comprises a proximal end and a distal end, B) a first filter comprising pores approximately 10-20 $\mu$m in size (e.g., about 10, 11, 12, 13, 14, 15, 16, 17, 18, 19, or 20 $\mu$m in size), positioned inside the vessel; C) a second filter comprising pores approximately 1-2 $\mu$m in size (e.g., about 1.0, 1.1, 1.2, 1.3, 1.4, 1.5, 1.6, 1.7, 1.8, 1.0, or 2.0 $\mu$m in size), positioned inside the vessel and distal to the first filter; and D) a third filter comprising pores approximately 0.1 $\mu$m in size (e.g., 0.05, 0.06, 0.07, 0.08, 0.09, 0.1, 0.11, 0.12, 0.13, 0.14, 0.15, or 0.16 $\mu$m in size), positioned inside the vessel distal to the first and second filters; wherein the first, second, and third filters are further positioned inside the sample containment vessel such that fluid passing from the proximal end to the distal end of the sample containment vessel passes through the first, second, and third filters; and b) pouring the sample into the proximal end of the sample containment vessel and treating the multi-stage purification device such that a purified sample is collected in, or eluted from, the distal end of the sample containment vessel, wherein the purified sample is free or 99% free of the human cells and comprises at least a portion of the pathogen nucleic acid if originally present in the sample.

In some embodiments, the present disclosure provides methods of purifying a sample comprising: a) providing: i) a sample comprising human cells and suspected of containing pathogens comprising pathogen nucleic acid; and ii) a multi-stage purification device comprising: A) a sample containment vessel (e.g., configured to be inserted into a centrifuge or agitation device), wherein the sample containment vessel comprises a proximal end and a distal end, B) a first filter comprising pores approximately 10-20 $\mu$m in size (e.g., about 10, 11, 12, 13, 14, 15, 16, 17, 18, 19, or 20 $\mu$m in size), positioned inside the vessel; C) a second filter comprising pores approximately 1-2 $\mu$m in size (e.g., about 1.0, 1.1, 1.2, 1.3, 1.4, 1.5, 1.6, 1.7, 1.8, 1.0, or 2.0 $\mu$m in size), positioned inside the vessel and distal to the first filter; D) a third filter comprising pores approximately 0.1 $\mu$m in size (e.g., 0.05, 0.06, 0.07, 0.08, 0.09, 0.1, 0.11, 0.12, 0.13, 0.14, 0.15, or 0.16 $\mu$m in size), positioned inside the vessel distal to the first and second filters; wherein the first, second, and third filters are further positioned inside the sample containment vessel such that fluid passing from the proximal end to the distal end of the sample containment vessel passes through the first, second, and third filters, and E) an affinity capture filter comprising affinity binding molecules, wherein said affinity capture filter is positioned inside said vessel distal to said first, second, and third filters, and further positioned such that said fluid passing from said open proximal end to said closed distal end of said sample containment vessel passes through said affinity capture filter; and b) pouring the sample into the proximal end of the sample containment vessel and treating the multi-stage purification device such that a purified sample is collected in, or eluted from, the distal end of the sample containment vessel, wherein the purified sample is free or 99% free of the human cells and comprises at least a portion of the pathogen nucleic acid if originally present in the sample.

In certain embodiments, the pathogen nucleic acid is bacterial, fungal, or viral nucleic acid or any mixture thereof. In certain embodiments, treating the multi-stage purification device comprises centrifuging or agitating the multi-stage purification device. In further embodiments, the centrifuging or agitating causes the third filter to mechanically shear at least some of the pathogens causing them to release the pathogen nucleic acid. In additional embodiments, the sample comprises whole blood.

In particular embodiments, only 1-2 mL of the sample is added to the multi-stage purification device. In other embodiments, the total volume of the purified sample is between 10-100 uL.

In particular embodiments, the present disclosure provides systems or devices for purifying microorganism (e.g., blood borne microorganism) nucleic acid from a sample comprising: i) a first size-exclusion filter that: excludes passage therethrough of lymphocytes, monocytes, neutrophils, eosinophils, and basophils (e.g., all from a human or other animal host), and allows passage therethrough of erythrocytes, lymphocytes, and platelets (e.g., all from a human or other animal host); ii) either: a) a second size-exclusion filter that: excludes passage therethrough of erythrocytes, lymphocytes, and platelets (e.g., all from a human or other animal host), and allows passage therethrough of microorganisms smaller than platelets (e.g., bacteria, virus, fungi, prions, etc.); or b) both of the following: I) a second size-exclusion filter that excludes passage therethrough of erythrocytes and lymphocytes (e.g., all from a human or other animal host), but allows passage therethrough of platelets and microorganisms smaller than platelets, and II) a third size-exclusion filter that excludes passage therethrough of platelets (e.g., human platelets), but allows passage therethrough of microorganisms smaller than platelets; and iii) a shearing filter that mechanically shears the microorganisms such that microorganism nucleic acid is released.

In some embodiments, the present disclosure provides systems or devices for purifying microorganism (e.g., blood borne microorganism) nucleic acid from a sample comprising: i) a first size-exclusion filter (e.g., with a pore size of about 10 $\mu$m) that: excludes passage therethrough of lymphocytes, monocytes, neutrophils, eosinophils, and basophils (e.g., all from a human or other animal host), and allows passage therethrough of erythrocytes, lymphocytes, and platelets (e.g., all from a human or other animal host); ii) either: a) a second size-exclusion filter that (e.g., with a pore size of about 2 μm): excludes passage therethrough of erythrocytes, lymphocytes, and platelets (e.g., all from a human or other animal host), and allows passage therethrough of microorganisms smaller than platelets (e.g., bacteria, virus, fungi, prions, etc.); or b) both of the following: I) a second size-exclusion filter (e.g., with a pore size of about 2 μm) that excludes passage therethrough of erythrocytes and lymphocytes (e.g., all from a human or other animal host), but allows passage therethrough of platelets and microorganisms smaller than platelets, and II) a third size-exclusion filter (e.g., with a pore size of about 2 μm) that excludes passage therethrough of platelets (e.g., human platelets), but allows passage therethrough of microorganisms smaller than platelets; iii) a shearing filter (e.g., with a pore size of about 0.1 μm) that mechanically shears the microorganisms such that microorganism nucleic acid is released; and, optionally, iv) an affinity capture filter comprising affinity binding molecules that bind human or animal nucleic acid (e.g., where the affinity binding molecules bind human repetitive nucleic acid sequences).

In some embodiments, the present disclosure provides systems or devices for purifying microorganism (e.g., blood borne microorganism) nucleic acid from a sample comprising: i) a first size-exclusion filter that: excludes passage therethrough of lymphocytes, monocytes, neutrophils, eosinophils, and basophils (e.g., all from a human or other animal host), and allows passage therethrough of erythrocytes, lymphocytes, and platelets (e.g., all from a human or other animal host); ii) either: a) a second size-exclusion filter that: excludes passage therethrough of erythrocytes, lymphocytes, and platelets (e.g., all from a human or other animal host), and allows passage therethrough of microorganisms smaller than platelets (e.g., bacteria, virus, fungi, prions, etc.); or b) both of the following: I) a second size-exclusion filter that excludes passage therethrough of erythrocytes and lymphocytes (e.g., all from a human or other animal host), but allows passage therethrough of platelets and microorganisms smaller than platelets, and II) a third size-exclusion filter that excludes passage therethrough of platelets (e.g., human platelets), but allows passage therethrough of microorganisms smaller than platelets; iii) a shearing filter that mechanically shears the microorganisms such that microorganism nucleic acid is released; and iv) a sample containment vessel, wherein the sample containment vessel comprises an proximal end and a distal end, and wherein said first and second size exclusion filters, and the third size exclusion filter if present, and the shearing filter, are located in the sample containment vessel.

In certain embodiments, the present invention provides a component selected from the group consisting of: a spin column, a plate filter, a filter manifold, and a microfluidic device, wherein the component further comprises: i) a first size-exclusion filter that: excludes passage therethrough of lymphocytes, monocytes, neutrophils, eosinophils, and basophils (e.g., all from a human or other animal host), and allows passage therethrough of erythrocytes, lymphocytes, and platelets (e.g., all from a human or other animal host); ii) either: a) a second size-exclusion filter that: excludes passage therethrough of erythrocytes, lymphocytes, and platelets (e.g., all from a human or other animal host), and allows passage therethrough of microorganisms smaller than platelets (e.g., bacteria, virus, fungi, prions, etc.); or b) both of the following: I) a second size-exclusion filter that excludes passage therethrough of erythrocytes and lymphocytes (e.g., all from a human or other animal host), but allows passage therethrough of platelets and microorganisms smaller than platelets, and II) a third size-exclusion filter that excludes passage therethrough of platelets (e.g., human platelets), but allows passage therethrough of microorganisms smaller than platelets; and iii) a shearing filter that mechanically shears the microorganisms such that microorganism nucleic acid is released.

In certain embodiments, the present disclosure provides methods for purifying microorganism (e.g., blood borne microorganism) nucleic acid from a sample comprising: a) moving a biological sample through a system or device, wherein the biological sample comprises human cells and is suspected of containing microorganisms, and wherein the system or device comprises: i) a first size-exclusion filter that: excludes passage therethrough of lymphocytes, monocytes, neutrophils, eosinophils, and basophils (e.g., all from a human or other animal host), and allows passage therethrough of erythrocytes, lymphocytes, and platelets (e.g., all from a human); ii) either: A) a second size-exclusion filter that: excludes passage therethrough of erythrocytes, lymphocytes, and platelets, and allows passage therethrough of microorganisms smaller than platelets; or B) both of the following: I) a second size-exclusion filter that excludes passage therethrough of erythrocytes and lymphocytes, but allows passage therethrough of platelets and microorganisms smaller than platelets, and II) a third size-exclusion filter that excludes passage therethrough of platelets (e.g., from a human or other animal host), but allows passage therethrough of microorganisms smaller than platelets (e.g., bacteria, virus, fungi, etc.); and iii) a shearing filter that mechanically shears the microorganisms such that microorganism nucleic acid is released; and b) collecting a purified sample in or from the system or device, wherein the purified sample is free or at least 99% free of the human cells and comprises at least a portion of the microorganism nucleic acid if microorganisms are originally present in the sample.

In some embodiments, the biological sample comprises whole blood (e.g., from an animal or human). In particular embodiments, the biological sample is moved through the system or device by: centrifugal force, positive pressure, or negative pressure.

In particular embodiments, the system or device further comprises an affinity capture filter comprising affinity binding molecules that bind human or animal nucleic acid. In further embodiments, the affinity binding molecules bind human repetitive nucleic acid sequences (e.g., repetitive nucleic acid sequence present in a centromere of a host chromosome, a repetitive nucleic acid sequence present in a telomere of a host chromosome, and a repetitive element, whether coding, non-coding, or intergenic, present in the host DNA). In particular embodiments, the affinity binding molecule bind the polyA tail on mRNA. In another embodiment, the affinity binding molecule binds high abundance transcripts in messenger RNA (mRNA) or the complementary DNA (cDNA) from those high abundance transcripts, or ribosomal RNA (rRNA) sequences.

In other embodiments, the first size-exclusion filter has a pore size of about 10 μm, or about 10-20 μm, or about 9-11 μm. In particular embodiments, the second size-exclusion filter of (ii) (a) has a pore size of about 2 μm (e.g., about 1-3 μm, about 1-2 μm, or about 1.8-2.2 μm). In certain embodiments, the second size-exclusion filter of (ii) (b) has a pore size of about 5 μm (e.g., about 3-7 μm, about 4-6 μm, or 4.6-5.4 μm) and the third size-exclusion filter has a pore size of about 2 μm (e.g., about 1-3 μm, about 1-2 μm, or about 1.8-2.2 μm). In particular embodiments, the shearing filter has a pore size of about 0.10 μm (e.g., about 0.05-0.25 μm or about 0.01-0.4 μm).

The filters described herein can be used in any and every combination in the devices, systems, and methods herein. For example, the devices and systems of the present invention may have only, or at least: the first size exclusion filter and the shearing filter; the second size-exclusion filter and the shearing filter; the third size-exclusion filter and the shearing filter; the first and second and/or third size exclusion filters; the second and third size exclusion filters and the shearing filter; or the first and third size exclusion filters and the shearing filter.

In some embodiments, the systems and devices further comprise a sample containment vessel, wherein the sample containment vessel comprises an proximal end and a distal end, and wherein the first and second size exclusion filters, and the third size exclusion filter if present, and the shearing filter, are located in the sample containment vessel. In further embodiments, the shearing filter is located distal to the second size exclusion filter, wherein the second size exclusion filter is located distal to the first size exclusion filter, and wherein the third size exclusion filter, if present, is located between the shearing filter and the second size exclusion filter. In other embodiments, the system or device is part of a component selected from the group consisting of: a spin column, a plate filter, a filter manifold, and a microfluidic device.

In certain embodiments, the present disclosure provides methods for purifying microorganism (e.g., blood borne microorganism) nucleic acid from a sample comprising: a) moving a biological sample through a system or device, wherein the biological sample comprises human cells and is suspected of containing microorganisms, and wherein the system or device comprises: i) a first size-exclusion filter that: excludes passage therethrough of lymphocytes, monocytes, neutrophils, eosinophils, and basophils (e.g., all from a human or other animal host), and allows passage therethrough of erythrocytes, lymphocytes, and platelets (e.g., all from a human); ii) either: A) a second size-exclusion filter that: excludes passage therethrough of erythrocytes, lymphocytes, and platelets, and allows passage therethrough of microorganisms smaller than platelets; or B) both of the following: I) a second size-exclusion filter that excludes passage therethrough of erythrocytes and lymphocytes, but allows passage therethrough of platelets and microorganisms smaller than platelets, and II) a third size-exclusion filter that excludes passage therethrough of platelets (e.g., from a human or other animal host), but allows passage therethrough of microorganisms smaller than platelets (e.g., bacteria, virus, fungi, etc.); iii) a shearing filter that mechanically shears the microorganisms such that microorganism nucleic acid is released; and iv) an affinity capture filter comprising affinity binding molecules that bind human or animal nucleic acid (e.g., where the affinity binding molecules bind human repetitive nucleic acid sequences); and b) collecting a purified sample in or from the system or device, wherein the purified sample is free or at least 99% free of the human cells and comprises at least a portion of the microorganism nucleic acid if microorganisms are originally present in the sample.

In certain embodiments, the present disclosure provides methods for purifying microorganism (e.g., blood borne microorganism) nucleic acid from a sample comprising: a) moving (e.g., centrifugal force, positive pressure, or negative pressure) a biological sample through a system or device that is part of a larger component (e.g., a spin column, a plate filter, a filter manifold, and a microfluidic device), wherein the biological sample comprises human cells and is suspected of containing microorganisms, and wherein the system or device comprises: i) a first size-exclusion filter that: excludes passage therethrough of lymphocytes, monocytes, neutrophils, eosinophils, and basophils (e.g., all from a human or other animal host), and allows passage therethrough of erythrocytes, lymphocytes, and platelets (e.g., all from a human); ii) either: A) a second size-exclusion filter that: excludes passage therethrough of erythrocytes, lymphocytes, and platelets, and allows passage therethrough of microorganisms smaller than platelets; or B) both of the following: I) a second size-exclusion filter that excludes passage therethrough of erythrocytes and lymphocytes, but allows passage therethrough of platelets and microorganisms smaller than platelets, and II) a third size-exclusion filter that excludes passage therethrough of platelets (e.g., from a human or other animal host), but allows passage therethrough of microorganisms smaller than platelets (e.g., bacteria, virus, fungi, etc.); iii) a shearing filter that mechanically shears the microorganisms such that microorganism nucleic acid is released; and iv) an affinity capture filter comprising affinity binding molecules that bind human or animal nucleic acid (e.g., where the affinity binding molecules bind human repetitive nucleic acid sequences); and b) collecting a purified sample in or from the system or device, wherein the purified sample is free or at least 99% free of the human cells and comprises at least a portion of the microorganism nucleic acid if microorganisms are originally present in the sample.

DEFINITIONS

As used herein, the term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable or can be made detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR) are forms of amplification. Amplification is not limited to the strict duplication of the starting molecule. For example, the generation of multiple cDNA molecules from a limited amount of RNA in a sample using reverse transcription (RT)-PCR is a form of amplification. Furthermore, the generation of multiple RNA molecules from a single DNA molecule during the process of transcription is also a form of amplification.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced (e.g., in the presence of nucleotides and an inducing agent such as a biocatalyst (e.g., a DNA polymerase or the like) and at a suitable temperature and pH). The primer is typically single stranded for maximum efficiency in amplification, but may alternatively be double stranded. If double stranded, the primer is generally first treated to separate its strands before being used to prepare extension products. In some embodiments, the primer is an oligodeoxyribonucleotide. The primer is sufficiently long to prime the synthesis of extension products in the presence of the inducing agent. The exact lengths of the primers will depend on many factors, including temperature, source of primer and the use of the method.

As used herein, the term "sample" refers to anything capable of being analyzed by the methods provided herein. In some embodiments, the sample comprises or is suspected to comprise one or more nucleic acids capable of analysis by the methods. Preferably, the samples comprise nucleic acids (e.g., DNA, RNA, cDNAs, etc.). Samples may be complex samples or mixed samples, which contain nucleic acids comprising multiple different nucleic acid sequences. Samples may comprise nucleic acids from more than one source (e.g. difference species, different subspecies, etc.), subject, and/or individual. In some embodiments, the methods provided herein comprise purifying the sample or purifying the nucleic acid(s) from the sample. In some embodiments, the sample contains purified nucleic acid. In some embodiments, a sample is derived from a biological, clinical, environmental, research, forensic, or other source.

"Enrichment" and "enriching" refer to an increase in and increasing, respectively, the proportion of nucleic acid from a microorganism (e.g., blood borne microorganism) relative to the remainder of the whole blood sample as the whole blood sample passes through the system and various components of the whole blood sample are excluded. The devices, systems, and methods of the present disclosure allow for enrichment of microorganism nucleic acid in a sample.

A "blood-borne microorganism" is intended to encompass any microorganism that can be found in blood. Examples of blood-borne microorganisms include bacteria, viruses, fungi, and parasites. A bacterium, which can be found in blood, can have the shape of a coccus, such as a coccus having a diameter from about 0.5 µm to about 1 µm, or a rod, such as a rod having a width from about 0.5 µm to about 1 µm and a length from about 1 µm to about 4 µm. A virus, which can be found in blood, can have a diameter, for example, from about 0.02 µm to about 0.3 µm. A fungus or parasite, which can be found in blood, can have a diameter from about 2 µm to about 10 µm.

In certain embodiments, a "whole blood sample" refers to an unprocessed sample of blood from an animal (e.g., human or blood containing animal). A preservative, such as ethylene diamine tetraacetic acid (EDTA), a citrate salt (e.g., sodium citrate), sodium azide, formalin, or thimerosal (thiomersal), may be added to the whole blood sample. An RNA preservative, such as RNAsin, RNAlater, or a ribonuclease inhibitor, may also be added to the sample to prevent RNA degradation; however, in certain embodiments, the systems, devices, and methods enrich DNA, in which case preservation of RNA is unnecessary. In addition, the whole blood sample may be diluted with a buffer, such as phosphate-buffered saline (PBS) or Tris-buffered saline (TBS), prior to introducing the whole blood sample into the systems or devices described herein. However, in particular embodiments, the whole blood sample is not otherwise processed, e.g., treated with a lytic agent to lyse cellular components, such as erythrocytes and leukocytes.

For purposes of the present disclosure, the diameter of an erythrocyte is estimated to be from about 6.5 µm to about 8 µm, the diameter of a leukocyte is estimated to be from about 6 µm to about 20 µm, and the diameter of a thrombocyte (or platelet) is estimated to be from about 2 µm to about 4 µm. More specifically, the diameter of a leukocyte can be further described with reference to a specific type of leukocyte. For example, the diameter of a lymphocyte is estimated to be from about 6 µm to about 18 µm, the diameter of a monocyte is estimated to be from about 12 µm to about 20 µm, the diameter of a neutrophil, an eosinophil, and a basophil is estimated to be from about 12 µm to about 15 µm.

DETAILED DESCRIPTION

The present disclosure provides systems, devices, and methods for purifying microorganism nucleic acid from a host sample, such as a whole blood sample from a human. In certain embodiments, devices and systems with multiple filters are employed and provide for the selective removal of blood cells and host nucleic acids from a sample in order to enrich for microorganism nucleic acid.

In certain embodiments, the volume of the sample (e.g., whole blood sample) introduced into the system or device depends, at least in part, on the size of the system or device. In general, the volume of the sample vis-à-vis the size of the system or device should not be so large as to clog one or more of the size-exclusion filters. If the system or device is part of a spin-column, for example, a volume of sample (e.g., whole blood) from, for example, about 1 mL to about 1.5 mL can be introduced into the system, or for larger spin-columns 5-7 mL can be introduced. In certain embodiments, if the volume of sample introduced into the system is about 1-2 mL, the volume of the final eluate (e.g., the enriched nucleic acid collected) can be a small fraction of the input volume (e.g., ~0.1).

Any suitable size-exclusion filter can be used in the systems and devices of the present disclosure. Examples of suitable size-exclusion filter manufacturers include, but are not limited to, Millipore, Whatman, Pall, and Nalgene. An example of a size-exclusion filter is nylon acetate, such as 0.2µ or 0.45µ nylon acetate (or a 0.2µ or 0.45µ cellulose acetate size exclusion filter).

In general, the porosity (i.e., size of the pores) of the size-exclusion filters decreases from the first filter to the last filter as sample travels through the devices or systems disclosed herein. In some embodiments, the porosity from one size-exclusion filter to the next size-exclusion filter can decrease by at least about 10-fold, such as about 15-fold or even about 20-fold. In certain embodiments, at least three size-exclusion filters, such as four size-exclusion filters or more, are used. In particular embodiments, when more filters are used, the decrease in porosity from one size-exclusion filter to the next size-exclusion filter may decrease by less, such as about 5-fold. For example, the first size-exclusion filter of can have a pore size of about 10 µm to about 20 µm, such as about 10 µm. The second size-exclusion filter can have a pore size of about 2 µm, or the second size-exclusion filter can have a pore size of about 5 µm and the third size-exclusion filter can have a pore size of about 2 µm. The shearing filter of can have a pore size of about 0.10 µm. In certain embodiments, the shearing filter is configured such that is can mechanically shear blood-borne microorganisms, such as bacteria and viruses. In particular embodiments, the methods do not use (and the devices and systems do not contain) one or more chemical lytic agents to lyse blood-borne microorganisms, such as bacteria and viruses.

Any suitable affinity capture layer can be used in the systems and devices disclosed herein. Examples of suitable DNA-derivatized affinity capture layers include, but are not limited to, DNA-cellulose, DNA-sepharose, DNA-silica, and DNA-latex (a polystyrene core with a glycidyl methacrylate surface). For more specific examples, see, e.g., cellulose acetate membranes by Whatman (see Whatman web site), cellulose acetate, cellulose nitrate, polytetrafluoroethylene (PTFE), polyethersulfone (PES), regenerated cellulose, polycarbonate, and polyamide membranes by Sartorius (see Sartorius web site), cellulose acetate and mixed cellulose ester (MCE) membranes by Advantec MFS, Inc. (see Advantec MFS web site), and cellulose acetate, PES, and MCE membranes by Membrane Solutions (see Membrane-Solutions web site). Other surfaces and membranes also can be employed (e.g., controlled-pore glass). Nucleic acid can be chemically derivatized and immobilized on these surfaces using, for example, amino, carboxyl, or another reactive group (e.g., covalent attachment chemistries).

In certain embodiments, the affinity capture layer binds a repetitive nucleic acid sequence present in the sample (e.g., whole blood sample). The repetitive nucleic acid sequence may be from the source of the whole blood sample (e.g., the animal, such as a mammal, e.g., a human, and not from the blood-borne microorganism). Examples of a repetitive nucleic acid sequence include a repetitive nucleic acid sequence present in a centromere of a host chromosome (or sequence fragment thereof), a repetitive nucleic acid sequence present in a telomere (or sub-telomeric region) of a host chromosome (or sequence fragment thereof), and a repetitive element, whether coding, non-coding, or intergenic, present in the host DNA. The repetitive nucleic acid sequence can be a polyA tail of mRNA. Specific examples of human repetitive nucleic acid include Alu repeat sequences, Cot-1 repeats, LINEs (long interspersed nuclear elements; e.g., LINE-1 and LINE-2), SINEs (short interspersed nuclear elements), satellite DNA or microsatellite DNA. In certain embodiments, the affinity capture layer binds more than one repetitive nucleic acid sequence, such as two, three, or even more repetitive nucleic acid sequences. When the affinity capture layer binds repetitive nucleic acid sequences that occur throughout the genome of the source of the sample (e.g., whole blood sample) the binding ability and binding capacity of the affinity capture membrane increases, and the enrichment of nucleic acid from a blood-borne microorganism present in the sample increases. Such repetitive nucleic acid sequences can be in the form of a pool of synthetic oligonucleotides, which can be derivatized as necessary and immobilized onto a solid support (e.g., DNA-cellulose, DNA-sepharose, DNA-silica, DNA-latex, and the like).

The sample (e.g., blood sample) can be moved through the systems and devices described herein by any suitable method. For example, the sample can be moved through the system by the application of centrifugal force, positive pressure, or negative pressure (e.g., vacuum aspiration). When centrifugal force is used, centrifugation time and relative centrifugal force (RCF) should be sufficient to effect passage of the sample through the system or device and result in collection of enriched nucleic acid from a blood-borne microorganism.

The systems and devices described herein can be part of a spin column, a plate filter, a filter manifold, or a microfluidic device, for example. The microfluidic device can be, for example, a microcapillary fluidic device. The system can be fabricated as part of the device or as a modular assembly that interfaces directly with the device or as a stand-alone, single-use component.

In certain embodiments, enriched or collected microorganism nucleic acid collected from the systems and devices described herein can be amplified prior to subsequent analysis, such as by whole genome amplification, rolling-circle replication, polymerase chain reaction (PCR), reverse-transcriptase PCR, or RNA amplification. In certain embodiments, the enriched eluate can be concentrated by ethanol precipitation, or further purified to afford a high-purity nucleic acid sample (e.g., by phenol chloroform extraction, paramagnetic bead capture and wash, DNA purification column, etc.). The enriched nucleic acid, which has been optionally amplified, can be subsequently analyzed by any method known in the art, examples of which include PCR, mass spectrometry, single nucleotide polymorphism (SNP) typing, DNA fingerprinting, and nucleic acid sequencing.

In certain embodiments, the systems and devices described herein can be used for next-generation real-time PCR. Alternatively, the systems and devices can be used to prepare samples for the Ibis platform (Ibis Biosciences, Carlsbad, Calif.; a subsidiary of Abbott Laboratories), thereby obviating the need for multiple extraction systems, reducing sample processing time, limiting the physical dimensions (i.e., footprint) of the system, and reducing labor associated with assay performance.

The methods, devices, systems described herein can be combined with other methods known in the art. For example, nucleic acid enriched/purified in accordance with the present disclosure can be concentrated and amplified in accordance with the method described in U.S. Pat. No. 7,807,360, which is specifically incorporated by reference for its teachings regarding a sequential concentration-amplification method.

In certain embodiments, the systems, devices, and methods described herein can be used to enrich nucleic acid from liquid or liquefied samples, such as plasma, buffy coat, lymphatic fluid, cerebrospinal fluid, sputum, bronchoalveolar lavage, fine needle aspirates, swabs (e.g., buccal, cervical, and nasal), interstitial fluid, synovial fluid, saliva, urine, breast milk, nasal discharge, and tears.

Figure 1:
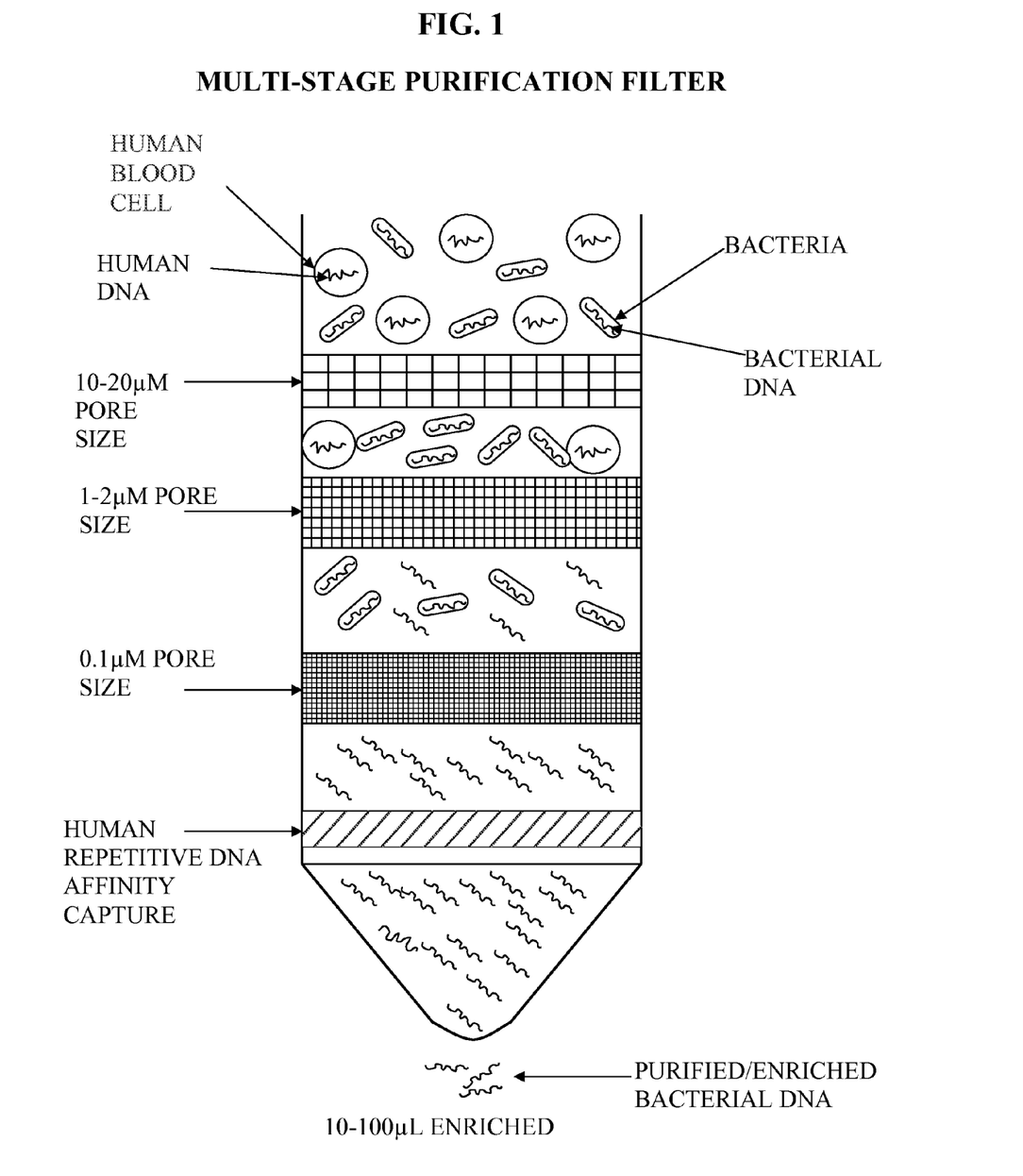
FIG. 1 provides an exemplary description of a multi-stage filter.

The present disclosure provides certain multi-stage purification filters and methods of using them (e.g., as shown in FIG. 1). In certain embodiments, the filters are employed in a single-step, multi-stage filtration process used in the purification/enrichment of bacterial, fungal, and viral DNA/RNA from a sample (e.g., whole blood), for subsequent molecular analysis. Such filters can be implemented in many embodiments, including, but not limited to: a spin-column, plate-filter, or filter-manifold assembly. In certain embodiments, the filters utilize a multi-stage series of size-exclusion filters of narrowing porosity (e.g., 3 or 4 stages, ~10-20μ to 0.1μ, in approximately 10-fold increments; see FIG. 1) to fractionate bacteria and viruses directly from a sample (e.g., whole blood), in a single-step. In certain embodiments, the multi-stage filter will also serve as a mechanical shearing surface/matrix for bacterial cell lysis. In other embodiments, the multi-stage filters include an affinity capture matrix, which, for example, may be loaded with human repetitive nucleic acid sequences (e.g., such as; Alu, Cot-1, LINEs, SINEs, centromeric and/or telomeric repeat sequences) to selectively bind and retain human nucleic acid sequences; thereby selectively enriching the specimen for bacterial, fungal and/or viral nucleic acid sequences that may be present in the sample (e.g., whole blood). In certain embodiments, the multi-stage filters are used to fractionate bacterial, fungal and viral DNA/RNA from a sample (e.g., 1-2 mL) without processing the entire sample; as an enriched small-volume eluate (e.g., 10-100 μL) obtained from the filter may provide adequate amounts of DNA for subsequent downstream molecular analysis (e.g., PCR, mass-spectrometry, etc.). In the event that the bacterial/fungal/viral DNA enriched eluate does not provide sufficient material for downstream analysis, the enriched bacterial/viral/fungal DNA may, for example, be amplified using conventional pre-amplification strategies (e.g., such as; whole genome amplification, rolling-circle replication, PCR, etc.). In other embodiments, the multi-stage filers are used to purify nucleic acid from RNA viruses, for direct analysis or intermediate amplification (e.g., Reverse-Trancriptase PCR or other RNA amplification methods).

FIG. 1 provides an exemplary description of a multi-stage filter, as used to purify nucleic acids from whole blood. As shown as the top of the figure, human erythrocytes and leukocytes are retained by an approximately 10-20μ pore, whereas bacterial, fungi, and viruses pass through down to a 1-2μ pore. The 1-2 u pore further purifies the sample and prevents human blood cells from passing through the pores. At least partial mechanical lysis of bacteria, fungi, and viruses, that have passed through the 1-2 u pore filter, can occur at the 0.1 u stage by mechanical shearing, allowing only nucleic acid to pass through the 0.1 u filter. The affinity step (e.g., containing human repetitive nucleic acid capture sequences) further enriches for the desired DNA/RNA target in the eluate by removing human nucleic acid sequences. One of skill in the art can optimize parameters to optimize the purification including the centrifugation time and relative centrifugal force (RCF), in order to accomplish the dual aims of retaining human cells in the upper stage(s) and lysing bacterial/fungal cells and viruses in the lower stage, prior to affinity enrichment. In certain embodiments, in order to accomplish these goals, only a fraction (e.g., 0.05 to 0.01) of a sample (e.g., whole blood specimen) needs to be fractioned through the multi-stage column.

The multi-step filters described herein could obviate the need for multiple extraction systems, reduce sample processing time, limit the systems physical dimensions (footprint), and reduce assay associated labor. Such columnbased front-end sample preparation/extraction may provide a universal solution for both systems like the IBIS mass spectrometry (base composition) platforms and next-generation Real Time-PCR systems.

Figure 2:
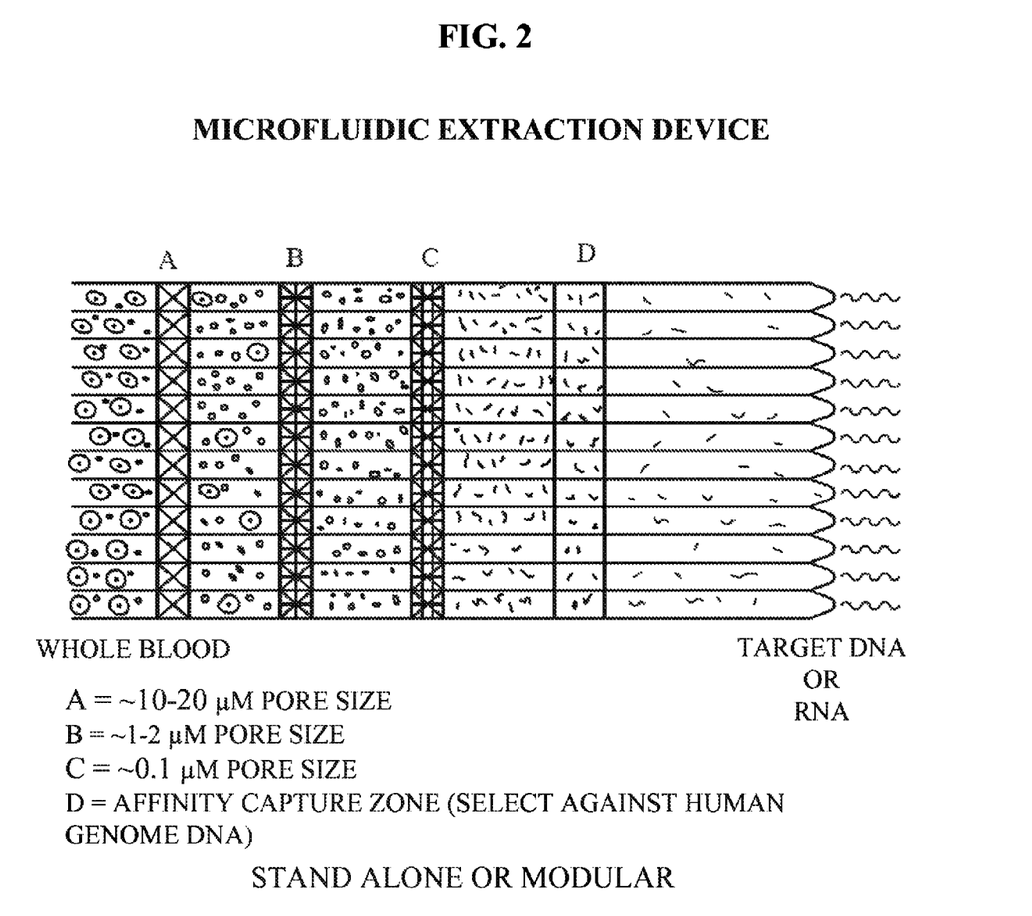
FIG. 2 shows an exemplary microfluidic extraction device with various pore sizes.

In other embodiments, provided herein is a microfluidic extraction device for purification and enrichment of total nucleic acid from whole blood (see, e.g., FIG. 2). In certain embodiments, the approach described herein employs a front-end microfluidic extraction device, that can be integrated into a microfluidic PCR system, to purify total nucleic acid from whole blood (e.g., human genomic DNA and blood-borne pathogens) as described above and in FIG. 1. In certain embodiments, a separation module can either be fabricated directly as part of the microfluidic device or linked as a modular assembly interfaced directly to a microfluidic PCR device, providing front-end sample preparation for the system. The device can also be a stand-alone, single-use component providing total nucleic acid for downstream molecular analysis. Microcapillary design utilizes a series of stages of narrowing porosity to filter the specimen and shear the sample. By controlling pore size, it is possible to design microcapilllaries composed of different channel architectures designed for specialized purification purposes (e.g., human, fungal, bacterial or viral DNA/RNA). The basic premise may be extended to include other liquid sample types such as serum, plasma, lymphatic fluid, interstitial fluid, cerebrospinal fluid (CSF), amniotic fluid, seminal fluid, vaginal excretions, serous fluid, synovial fluid, pericardial fluid, peritoneal fluid, pleural fluid, transudates, exudates, cystic fluid, bile, gastric fluids, intestinal fluids, saliva, urine, breast milk, and teardrops. Two advantages conferred by this approach include sample concentration and affinity-based selection against targets that are not of immediate interest (e.g., such as human DNA sequences, in the case of bacterial/viral pathogen detection). Together with the column-based sample preparation method and a PCR amplification/detection process, this approach provides a method for up-front sample preparation of total nucleic acid from whole blood and other fluids (e.g., plasma, lymphatic fluid, interstitial fluid, saliva, urine, breast milk and teardrops).

In certain embodiments, the isolated nucleic acid is subject to amplification. In some embodiments, fluorescence detection methods are provided for detection of amplified nucleic acid. In addition to the reagents already discussed, and those known to those of skill in the art of nucleic acid amplification and detection, various detection reagents, such as fluorescent and non-fluorescent dyes and probes are provided. For example, the protocols may employ reagents suitable for use in a TaqMan reaction, such as a TaqMan probe; reagents suitable for use in a SYBR Green fluorescence detection; reagents suitable for use in a molecular beacon reaction, such as molecular beacon probes; reagents suitable for use in a scorpion reaction, such as a scorpion probe; reagents suitable for use in a fluorescent DNA-binding dye-type reaction, such as a fluorescent probe; and/or reagents for use in a LightUp protocol, such as a LightUp probe. In some embodiments, provided herein are methods and compositions for detecting and/or quantifying a detectable signal (e.g. fluorescence) from purified samples containing amplified target nucleic acid. Thus, for example, methods may employ labeling (e.g. during amplification, post-amplification) amplified nucleic acids with a detectable label, exposing partitions to a light source at a wavelength selected to cause the detectable label to fluoresce, and detecting and/or measuring the resulting fluorescence. Fluorescence emitted from the samples can be tracked during amplification reaction to permit monitoring of the reaction (e.g., using a SYBR Green-type compound), or fluorescence can be measure post-amplification.

In some embodiments, detection of amplified nucleic acids employs one or more of fluorescent labeling, fluorescent intercalation dyes, FRET-based detection methods (U.S. Pat. No. 5,945,283; PCT Publication WO 97/22719; both of which are incorporated by reference in their entireties), quantitative PCR, real-time fluorogenic methods (U.S. Pat. No. 5,210,015 to Gelfand, U.S. Pat. No. 5,538,848 to Livak, et al., and U.S. Pat. No. 5,863,736 to Haaland, as well as Heid, C. A., et al., Genome Research, 6:986-994 (1996); Gibson, U. E. M, et al., Genome Research 6:995-1001 (1996); Holland, P. M., et al., Proc. Natl. Acad. Sci. USA 88:7276-7280, (1991); and Livak, K. J., et al., PCR Methods and Applications 357-362 (1995), each of which is incorporated by reference in its entirety), molecular beacons (Piatek, A. S., et al., Nat. Biotechnol. 16:359-63 (1998); Tyagi, S. and Kramer, F. R., Nature Biotechnology 14:303-308 (1996); and Tyagi, S. et al., Nat. Biotechnol. 16:49-53 (1998); herein incorporated by reference in their entireties), Invader assays (Third Wave Technologies, (Madison, Wis.)) (Keri, B. P., et al., Advances in Nucleic Acid and Protein Analysis 3826:117-125, 2000; herein incorporated by reference in its entirety), nucleic acid sequence-based amplification (NASBA; (See, e.g., Compton, J. Nucleic Acid Sequence-based Amplification, Nature 350: 91-91, 1991; herein incorporated by reference in its entirety), Scorpion probes (Thelwell, et al. Nucleic Acids Research, 28:3752-3761, 2000; herein incorporated by reference in its entirety), capacitive DNA detection (See, e.g., Sohn, et al. (2000)

Proc. Natl. Acad. Sci. U.S.A. 97:10687-10690; herein incorporated by reference in its entirety), etc.

Amplified nucleic acid molecules may be analyzed by any number of techniques to determine the presence of, amount of, or identity of the molecule. Non-limiting examples include sequencing, mass determination, and base composition determination. The analysis may identify the sequence of all or a part of the amplified nucleic acid or one or more of its properties or characteristics to reveal the desired information. For example, in some embodiments, the presence of a polymorphism is determined, for example, to provide information about the nature of an organism (e.g., pathogen), a disease state, a metabolic state, and the like. In some embodiments, the methylation status of a nucleic acid is determined. In some such embodiments, a target nucleic acid may be chemically modified (e.g., via bisulfite treatment) prior to amplification to create a marker for the methylation sites.

Illustrative non-limiting examples of nucleic acid sequencing techniques include, but are not limited to, chain terminator (Sanger) sequencing and dye terminator sequencing, as well as "next generation" sequencing techniques. Those of ordinary skill in the art will recognize that because RNA is less stable in the cell and more prone to nuclease attack experimentally RNA is usually, although not necessarily, reverse transcribed to DNA before sequencing.

A number of DNA sequencing techniques are known in the art, including fluorescence-based sequencing methodologies (See, e.g., Birren et al., Genome Analysis: Analyzing DNA, 1, Cold Spring Harbor, N.Y.; herein incorporated by reference in its entirety). In some embodiments, automated sequencing techniques understood in that art are utilized. In some embodiments, the systems, devices, and methods employ parallel sequencing of partitioned amplicons (PCT Publication No: WO2006084132 to Kevin McKernan et al., herein incorporated by reference in its entirety). In some embodiments, DNA sequencing is achieved by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques include the Church polony technology (Mitra et al., 2003, Analytical Biochemistry 320, 55-65; Shendure et al., 2005 Science 309, 1728-1732; U.S. Pat. No. 6,432,360, U.S. Pat. No. 6,485,944, U.S. Pat. No. 6,511,803; herein incorporated by reference in their entireties) the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. No. 6,787,308; U.S. Pat. No. 6,833,246; herein incorporated by reference in their entireties), the Lynx massively parallel signature sequencing technology (Brenner et al. (2000). Nat. Biotechnol. 18:630-634; U.S. Pat. No. 5,695,934; U.S. Pat. No. 5,714,330; herein incorporated by reference in their entireties) and the Adessi PCR colony technology (Adessi et al. (2000). Nucleic Acid Res. 28, E87; WO 00018957; herein incorporated by reference in its entirety).

In some embodiments, chain terminator sequencing is utilized. Chain terminator sequencing uses sequence-specific termination of a DNA synthesis reaction using modified nucleotide substrates. Extension is initiated at a specific site on the template DNA by using a short radioactive, or other labeled, oligonucleotide primer complementary to the template at that region. The oligonucleotide primer is extended using a DNA polymerase, standard four deoxynucleotide bases, and a low concentration of one chain terminating nucleotide, most commonly a di-deoxynucleotide. This reaction is repeated in four separate tubes with each of the bases taking turns as the di-deoxynucleotide. Limited incorporation of the chain terminating nucleotide by the DNA polymerase results in a series of related DNA fragments that are terminated only at positions where that particular di-deoxynucleotide is used. For each reaction tube, the fragments are size-separated by electrophoresis in a slab polyacrylamide gel or a capillary tube filled with a viscous polymer. The sequence is determined by reading which lane produces a visualized mark from the labeled primer as you scan from the top of the gel to the bottom.

Dye terminator sequencing alternatively labels the terminators. Complete sequencing can be performed in a single reaction by labeling each of the di-deoxynucleotide chain-terminators with a separate fluorescent dye, which fluoresces at a different wavelength.

A set of methods referred to as "next-generation sequencing" techniques have emerged as alternatives to Sanger and dye-terminator sequencing methods (Voelkerding et al., Clinical Chem., 55: 641-658, 2009; MacLean et al., Nature Rev. Microbiol., 7: 287-296; each herein incorporated by reference in their entirety). Next-generation sequencing (NGS) methods share the common feature of massively parallel, high-throughput strategies, with the goal of lower costs in comparison to older sequencing methods. NGS methods can be broadly divided into those that require template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., and Pacific Biosciences, respectively.

In pyrosequencing (Voelkerding et al., Clinical Chem., 55: 641-658, 2009; MacLean et al., Nature Rev. Microbiol., 7: 287-296; U.S. Pat. No. 6,210,891; U.S. Pat. No. 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotiter plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $1 \times 10^6$ sequence reads can be achieved, resulting in up to 500 million base pairs (Mb) of sequence.

In the Solexa/Illumina platform (Voelkerding et al., Clinical Chem., 55: 641-658, 2009; MacLean et al., Nature Rev. Microbiol., 7: 287-296; U.S. Pat. No. 6,833,246; U.S. Pat. No. 7,115,400; U.S. Pat. No. 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLiD technology (Voelkerding et al., *Clinical Chem.*, 55: 641-658, 2009; MacLean et al., *Nature Rev. Microbiol.*, 7: 287-296; U.S. Pat. No. 5,912,148; U.S. Pat. No. 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color and thus identity of each probe corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, nanopore sequencing in employed (see, e.g., Astier et al., J Am Chem Soc. 2006 Feb. 8; 128(5):1705-10, herein incorporated by reference). The theory behind nanopore sequencing has to do with what occurs when the nanopore is immersed in a conducting fluid and a potential (voltage) is applied across it: under these conditions a slight electric current due to conduction of ions through the nanopore can be observed, and the amount of current is exceedingly sensitive to the size of the nanopore. If DNA molecules pass (or part of the DNA molecule passes) through the nanopore, this can create a change in the magnitude of the current through the nanopore, thereby allowing the sequences of the DNA molecule to be determined.

Another exemplary nucleic acid sequencing approach that may be adapted for use with the systems, devices, and methods was developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Patent Publication No. 20090035777, entitled "HIGH THROUGHPUT NUCLEIC ACID SEQUENCING BY EXPANSION," that was filed Jun. 19, 2008, which is incorporated herein in its entirety.

Other emerging single molecule sequencing methods include real-time sequencing by synthesis using a VisiGen platform (Voelkerding et al., *Clinical Chem.*, 55: 641-658, 2009; U.S. Pat. No. 7,329,492; U.S. patent application Ser. No. 11/671,956; U.S. patent application Ser. No. 11/781, 166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition.

Processes and systems for such real time sequencing that may be adapted for use with the invention are described in, for example, U.S. Pat. No. 7,405,281, entitled "Fluorescent nucleotide analogs and uses therefor", issued Jul. 29, 2008 to Xu et al., U.S. Pat. No. 7,315,019, entitled "Arrays of optical confinements and uses thereof", issued Jan. 1, 2008 to Turner et al., U.S. Pat. No. 7,313,308, entitled "Optical analysis of molecules", issued Dec. 25, 2007 to Turner et al., U.S. Pat. No. 7,302,146, entitled "Apparatus and method for analysis of molecules", issued Nov. 27, 2007 to Turner et al., and U.S. Pat. No. 7,170,050, entitled "Apparatus and methods for optical analysis of molecules", issued Jan. 30, 2007 to Turner et al., U.S. Patent Publications Nos. 20080212960, entitled "Methods and systems for simultaneous real-time monitoring of optical signals from multiple sources", filed Oct. 26, 2007 by Lundquist et al., 20080206764, entitled "Flowcell system for single molecule detection", filed Oct. 26, 2007 by Williams et al., 20080199932, entitled "Active surface coupled polymerases", filed Oct. 26, 2007 by Hanzel et al., 20080199874, entitled "CONTROLLABLE STRAND SCISSION OF MINI CIRCLE DNA", filed Feb. 11, 2008 by Otto et al., 20080176769, entitled "Articles having localized molecules disposed thereon and methods of producing same", filed Oct. 26, 2007 by Rank et al., 20080176316, entitled "Mitigation of photodamage in analytical reactions", filed Oct. 31, 2007 by Eid et al., 20080176241, entitled "Mitigation of photodamage in analytical reactions", filed Oct. 31, 2007 by Eid et al., 20080165346, entitled "Methods and systems for simultaneous real-time monitoring of optical signals from multiple sources", filed Oct. 26, 2007 by Lundquist et al., 20080160531, entitled "Uniform surfaces for hybrid material substrates and methods for making and using same", filed Oct. 31, 2007 by Korlach, 20080157005, entitled "Methods and systems for simultaneous real-time monitoring of optical signals from multiple sources", filed Oct. 26, 2007 by Lundquist et al., 20080153100, entitled "Articles having localized molecules disposed thereon and methods of producing same", filed Oct. 31, 2007 by Rank et al., 20080153095, entitled "CHARGE SWITCH NUCLEOTIDES", filed Oct. 26, 2007 by Williams et al., 20080152281, entitled "Substrates, systems and methods for analyzing materials", filed Oct. 31, 2007 by Lundquist et al., 20080152280, entitled "Substrates, systems and methods for analyzing materials", filed Oct. 31, 2007 by Lundquist et al., 20080145278, entitled "Uniform surfaces for hybrid material substrates and methods for making and using same", filed Oct. 31, 2007 by Korlach, 20080128627, entitled "SUBSTRATES, SYSTEMS AND METHODS FOR ANALYZING MATERIALS", filed Aug. 31, 2007 by Lundquist et al., 20080108082, entitled "Polymerase enzymes and reagents for enhanced nucleic acid sequencing", filed Oct. 22, 2007 by Rank et al., 20080095488, entitled "SUBSTRATES FOR PERFORMING ANALYTICAL REACTIONS", filed Jun. 11, 2007 by Foquet et al., 20080080059, entitled "MODULAR OPTICAL COMPONENTS AND SYSTEMS INCORPORATING SAME", filed Sep. 27, 2007 by Dixon et al., 20080050747, entitled "Articles having localized molecules disposed thereon and methods of producing and using same," filed Aug. 14, 2007 by Korlach et al., 20080032301, entitled "Articles having localized molecules disposed thereon and methods of producing same", filed Mar. 29, 2007 by Rank et al., 20080030628, entitled "Methods and systems for simultaneous real-time monitoring of optical signals from multiple sources", filed Feb. 9, 2007 by Lundquist et al., 20080009007, entitled "CONTROLLED INITIATION OF PRIMER EXTENSION", filed Jun. 15, 2007 by Lyle et al., 20070238679, entitled "Articles having localized molecules disposed thereon and methods of producing same", filed Mar. 30, 2006 by Rank et al., 20070231804, entitled "Methods, systems and compositions for monitoring enzyme activity and applications thereof", filed Mar. 31, 2006 by Korlach et al., 20070206187, entitled "Methods and systems for simultaneous real-time monitoring of optical signals from multiple sources", filed Feb. 9, 2007 by Lundquist et al., 20070196846, entitled "Polymerases for nucleotide analogue incorporation", filed Dec. 21, 2006 by Hanzel et al., 20070188750, entitled "Methods and systems for simultaneous real-time monitoring of optical signals from multiple sources", filed Jul. 7, 2006 by Lundquist et al., 20070161017, entitled "MITIGATION OF PHOTODAMAGE IN ANALYTICAL REACTIONS", filed Dec. 1, 2006 by Eid et al., 20070141598, entitled "Nucleotide Compositions and Uses Thereof", filed Nov. 3, 2006 by Turner et al., 20070134128, entitled "Uniform surfaces for hybrid material substrate and methods for making and using same", filed Nov. 27, 2006 by Korlach, 20070128133, entitled "Mitigation of photodamage in analytical reactions", filed Dec. 2, 2005 by Eid et al., 20070077564, entitled "Reactive surfaces, substrates and methods of producing same", filed Sep. 30, 2005 by Roitman et al., 20070072196, entitled "Fluorescent nucleotide analogs and uses therefore", filed Sep. 29, 2005 by Xu et al. and 20070036511, entitled "Methods and systems for monitoring multiple optical signals from a single source", filed Aug. 11, 2005 by Lundquist et al., and Korlach et al. (2008) "Selective aluminum passivation for targeted immobilization of single DNA polymerase molecules in zero-mode waveguide nanostructures" Proc. Nat'l. Acad. Sci. U.S.A. 105(4): 11761181—all of which are herein incorporated by reference in their entireties.

In some embodiments, nucleic acids are analyzed by determination of their mass and/or base composition. For example, in some embodiments, nucleic acids are detected and characterized by the identification of a unique base composition signature (BCS) using mass spectrometry (e.g., Abbott PLEX-ID system, Abbott Ibis Biosciences, Abbott Park, Ill.,) described in U.S. Pat. Nos. 7,108,974, 8,017,743, and 8,017,322; each of which is herein incorporated by reference in its entirety.

In some embodiments, a MassARRAY system (Sequenom, San Diego, Calif.) is used to detect or analyze sequences (See e.g., U.S. Pat. Nos. 6,043,031; 5,777,324; and 5,605,798; each of which is herein incorporated by reference).

Samples may be derived from any suitable source, and for purposes related to any field, including but not limited to diagnostics, research, forensics, epidemiology, pathology, archaeology, etc. A sample may be biological, environmental, forensic, veterinary, clinical, etc. in origin. Samples may include nucleic acid derived from any suitable source, including eukaryotes, prokaryotes (e.g. infectious bacteria), mammals, humans, non-human primates, canines, felines, bovines, equines, porcines, mice, viruses, etc. Samples may contain, e.g., whole organisms, organs, tissues, cells, organelles (e.g., chloroplasts, mitochondria), synthetic nucleic acid, cell lysate, etc. Nucleic acid present in a sample (e.g. target nucleic acid, template nucleic acid, non-target nucleic acid, contaminant nucleic acid may be of any type, e.g., genomic DNA, RNA, microRNA, mitochondrial DNA, plasmids, bacteriophages, viruses, synthetic origin, natural origin, and/or artificial sequences (non-naturally occurring), synthetically-produced but naturally occurring sequences, etc. Biological specimens may, for example, include whole blood, lymphatic fluid, serum, plasma, sweat, tear, saliva, sputum, cerebrospinal (CSF) fluids, amniotic fluid, seminal fluid, vaginal excretions, serous fluid, synovial fluid, pericardial fluid, peritoneal fluid, pleural fluid, transudates, exudates, cystic fluid, bile, urine, gastric fluids, intestinal fluids, fecal samples, aspirates (bone marrow, fine needle) and swabs or washes (e.g., oral, nasopharangeal, bronchial, bronchioalveolar, optic, rectal, intestinal, vaginal, epidermal, etc.) and/or other fresh, frozen, cultured, preserved (PAXgene™, RNAlater™, RNasin®, etc.) or archived biological specimens (formalin fixed paraffin-embedded (FFPE), fixed cell/lymphocyte pellet, etc.).

In some embodiments, samples are mixed samples (e.g. containing mixed nucleic acid populations). In some embodiments, samples analyzed by methods herein contain, or may contain, a plurality of different nucleic acid sequences. In some embodiments, a sample (e.g. mixed sample) contains one or more nucleic acid molecules (e.g. 1 . . . 10 . . . $10^2$ . . . $10^3$ . . . $10^4$ . . . $10^5$ . . . $10^6$ . . . $10^7$, etc.) that contain a target sequence of interest in a particular application. In some embodiments, a sample (e.g. mixed sample) contains zero nucleic acid molecules that contain a target sequence of interest in a particular application. In some embodiments, a sample (e.g. mixed sample) contains nucleic acid molecules with a plurality of different sequences that all contain a target sequence of interest. In some embodiments, a sample (e.g. mixed sample) contains one or more nucleic acid molecules (e.g. 1 . . . 10 . . . $10^2$ . . . $10^3$ . . . $10^4$ . . . $10^5$ . . . $10^6$ . . . $10^7$, etc.) that do not contain a target sequence of interest in a particular application. In some embodiments, a sample (e.g. mixed sample) contains zero nucleic acid molecules that do not contain a target sequence of interest in a particular application. In some embodiments, a sample (e.g. mixed sample) contains nucleic acid molecules with a plurality of different sequences that do not contain a target sequence of interest. In some embodiments, a sample contains more nucleic acid molecules that do not contain a target sequence than nucleic acid molecules that do contain a target sequence (e.g. 1.01:1 . . . 2:1 . . . 5:1 . . . 10:1 . . . 20:1 . . . 50:1 . . . $10^2$:1 . . . $10^3$:1 . . . $10^4$:1 . . . $10^5$:1 . . . $10^6$:1 . . . $10^7$:1). In some embodiments, a sample contains more nucleic acid molecules that do contain a target sequence than nucleic acid molecules that do not contain a target sequence (e.g. 1.01:1 . . . 2:1 . . . 5:1 . . . 10:1 . . . 20:1 . . . 50:1 . . . $10^2$:1 . . . $10^3$:1 . . . $10^4$:1 . . . $10^5$:1 . . . $10^6$:1 . . . $10^7$:1). In some embodiments, a sample contains a single target sequence that may be present in one or more nucleic acid molecules in the sample. In some embodiments, a sample contains two or more target sequences (e.g. 2, 3, 4, 5 . . . 10 . . . 20 . . . 50 . . . 100, etc.) that may each be present in one or more nucleic acid molecules in the sample.

In some embodiments, various sample processing steps may be accomplished to prepare the nucleic acid molecules within a sample, including, but not limited to cell lysis, restriction digestion, purification, precipitation, resuspension (e.g. in amplification buffer), dialysis, etc. In some embodiments, sample processing is performed before or after any of the steps including, but not limited to partitioning, amplification, re-amplification), amplicon detection, amplicon isolation, sequencing, etc.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claim.

We claim:

1. A device comprising:
    i) a first size-exclusion filter that: excludes passage therethrough of monocytes, neutrophils, eosinophils, and basophils, and allows passage therethrough of erythrocytes, lymphocytes, and platelets;
    ii) either:
        a) a second size-exclusion filter that: excludes passage therethrough of erythrocytes, lymphocytes, and platelets, and allows passage therethrough of microorganisms smaller than platelets; or
        b) both of the following:
            I) a second size-exclusion filter that excludes passage therethrough of erythrocytes and lymphocytes, but allows passage therethrough of platelets and microorganisms smaller than platelets, and
            II) a third size-exclusion filter that excludes passage therethrough of platelets, but allows passage therethrough of blood-borne microorganisms smaller than platelets;
    iii) a shearing filter that mechanically shears said blood-borne microorganisms such that blood-borne microorganism nucleic acid is released wherein said shearing filter has a pore size of 0.05-0.25 µm; and
    iv) a sample containment vessel comprising a proximal end and a distal end, wherein said first and second size exclusion filters, and said third size exclusion filter if present, and said shearing filter, are located inside said sample containment vessel such that fluid passing from said proximal end to said distal end of said sample containment vessel passes through said first size exclusion filter first, said second size exclusion filter second, and said third size exclusion filter third if present, wherein said distal end of said sample containment vessel is configured for collection or elution of a purified sample, and wherein said sample containment vessel comprises a purified sample at said distal end comprising said blood borne microorganism nucleic acid free of genomic human or animal nucleic acid.

2. The device of claim 1, further comprising v) an affinity capture filter comprising affinity binding molecules that bind human repetitive nucleic acid sequences, wherein said affinity capture filter is located inside said sample containment vessel distal to said shearing filter.

3. The device of claim 1, wherein said first size-exclusion filter has a pore size of 9-11 µm.

4. The device of claim 1, wherein the second size-exclusion filter of (ii) (a) has a pore size of 1-3 µm or wherein the second size-exclusion filter of (ii) (b) has a pore size of 3-7 µm and the third size-exclusion filter has a pore size of 1-3 µm.

5. The device of claim 1, wherein said sample containment vessel has a tube-type shape.

6. A system comprising:
    i) a first size-exclusion filter that: excludes passage therethrough of monocytes, neutrophils, eosinophils, and basophils, and allows passage therethrough of erythrocytes, lymphocytes, and platelets;
    ii) either:
        a) a second size-exclusion filter that: excludes passage therethrough of erythrocytes, lymphocytes, and platelets, and allows passage therethrough of microorganisms smaller than platelets; or
        b) both of the following:
            I) a second size-exclusion filter that excludes passage therethrough of erythrocytes and lymphocytes, but allows passage therethrough of platelets and microorganisms smaller than platelets, and
            II) a third size-exclusion filter that excludes passage therethrough of platelets, but allows passage therethrough of blood-borne microorganisms smaller than platelets;
    iii) a shearing filter that mechanically shears said blood-borne microorganisms such that blood-borne microorganism nucleic acid is released wherein said shearing filter has a pore size of 0.05-0.25 µm; and
    iv) a sample containment vessel comprising a proximal end and a distal end, wherein said first and second size exclusion filters, and said third size exclusion filter if present, and said shearing filter, are located inside said sample containment vessel such that fluid passing from said proximal end to said distal end of said sample containment vessel passes through said first size exclusion filter first, said second size exclusion filter second, and said third size exclusion filter third if present, wherein said distal end of said sample containment vessel is configured for collection or elution of a purified sample, and wherein said sample containment vessel comprises a purified sample at said distal end comprising said blood borne microorganism nucleic acid free of genomic human or animal nucleic acid.

7. The system of claim 6, further comprising v) an affinity capture filter comprising affinity binding molecules that bind human repetitive nucleic acid sequences, wherein said affinity capture filter is located inside said sample containment vessel distal to said shearing filter.

8. The system of claim 6, wherein said first size-exclusion filter has a pore size of 9-11 µm.

9. The system of claim 6, wherein the second size-exclusion filter of (ii) (a) has a pore size of 1-3 µm or wherein the second size-exclusion filter of (ii) (b) has a pore size of 3-7 µm and the third size-exclusion filter has a pore size of 1-3 µm.

10. The system of claim 6, wherein said sample containment vessel has a tube-type shape.

11. A device, comprising:
   i) a first upper size-exclusion filter with a pore size of 10-20 µm;
   ii) either:
      a) a second size-exclusion filter with a pore size of 1-3 µm distal to said first upper size exclusion filter; or
      b) both of the following:
         I) a second size-exclusion filter with a pore size of 3-7 µm distal to said first upper size exclusion filter; and
         II) a third size-exclusion filter with a pore size of 1-3 µm distal to said second size exclusion filter;
   iii) a shearing filter with a pore size of 0.05-0.25 µm distal to said second or to said third size exclusion filter;
   iv) an affinity capture filter comprising affinity binding molecules that bind human repetitive nucleic acid sequences distal to said shearing filter;
   v) a sample containment vessel comprising a proximal end and a distal end, wherein said first and second size exclusion filters, and said third size exclusion filter if present, said shearing filter, and said affinity capture filter are located inside said sample containment vessel wherein said distal end of said sample containment vessel is configured for collection or elution of a purified sample, and wherein said sample containment vessel comprises a purified sample at said distal end comprising said blood borne microorganism nucleic acid free of genomic human or animal nucleic acid.

12. A system, comprising:
   i) a first upper size-exclusion filter with a pore size of 10-20 µm;
   ii) either:
      a) a second size-exclusion filter with a pore size of 1-3 µm distal to said first upper size exclusion filter; or
      b) both of the following:
         I) a second size-exclusion filter with a pore size of 3-7 µm distal to said first upper size exclusion filter; and
         II) a third size-exclusion filter with a pore size of 1-3 µm distal to said second size exclusion filter;
   iii) a shearing filter with a pore size of 0.05-0.25 µm distal to said second or to said third size exclusion filter;
   iv) an affinity capture filter comprising affinity binding molecules that bind human repetitive nucleic acid sequences distal to said shearing filter;
   v) a sample containment vessel comprising a proximal end and a distal end, wherein said first and second size exclusion filters, and said third size exclusion filter if present, said shearing filter, and said affinity capture filter are located inside said sample containment vessel wherein said distal end of said sample containment vessel is configured for collection or elution of a purified sample, and wherein said sample containment vessel comprises a purified sample at said distal end comprising said blood borne microorganism nucleic acid free of genomic human or animal nucleic acid.

13. The device of claim 11, wherein said device does not contain a chemical lytic agent.

14. The system of claim 12, wherein said system does not contain a chemical lytic agent.

\* \* \* \* \*

UNITED STATES PATENT AND TRADEMARK OFFICE
CERTIFICATE OF CORRECTION

PATENT NO.         : 9,855,559 B2
APPLICATION NO.    : 13/724527
DATED              : January 2, 2018
INVENTOR(S)        : Herbert A. Marble and Thomas Laffler Page 1 of 1

It is certified that error appears in the above-identified patent and that said Letters Patent is hereby corrected as shown below:

In the Claims

Claim 6, Column, 22, Line 37 reads:
"microorganisms smaller than platelets, and"
Whereas it should read:
"blood-borne microorganisms smaller than platelets, and"

Claim 6, Column, 22, Line 59 reads:
"comprising said blood borne microorganism nucleic"
Whereas it should read:
"comprising blood-borne microorganism nucleic"

Claim 11, Column, 23, Line 34 reads:
"comprising said blood borne microorganism nucleic"
Whereas it should read:
"comprising blood-borne microorganism nucleic"

Claim 12, Column, 24, Line 28 reads:
"comprising said blood borne microorganism nucleic"
Whereas it should read:
"comprising blood-borne microorganism nucleic"

Signed and Sealed this
Twentieth Day of November, 2018

Andrei Iancu
*Director of the United States Patent and Trademark Office*